(12) United States Patent
Doe

(10) Patent No.: US 7,526,941 B2
(45) Date of Patent: May 5, 2009

(54) RHEOMETER TORQUE CALIBRATION FIXTURE

(75) Inventor: Nigel Doe, Horsham (GB)

(73) Assignee: Waters Investments Limited, New Castle, DE (US)

( * ) Notice: Subject to any disclaimer, the term of this patent is extended or adjusted under 35 U.S.C. 154(b) by 139 days.

(21) Appl. No.: 11/762,375

(22) Filed: Jun. 13, 2007

(65) Prior Publication Data

US 2007/0295055 A1    Dec. 27, 2007

Related U.S. Application Data

(60) Provisional application No. 60/815,566, filed on Jun. 22, 2006.

(51) Int. Cl.
  *G01N 21/00*    (2006.01)
(52) U.S. Cl. ..................................................... 73/1.02
(58) Field of Classification Search .................. 73/1.02, 73/1.03, 1.11
  See application file for complete search history.

(56) References Cited

U.S. PATENT DOCUMENTS

| | | | |
|---|---|---|---|
| 4,630,468 A | 12/1986 | Sweet | 73/54.33 |
| 4,794,788 A * | 1/1989 | Masters et al. | 73/54.27 |
| 4,878,377 A | 11/1989 | Abel | 73/54.32 |
| 5,777,212 A | 7/1998 | Sekiguchi et al. | 73/54.43 |
| 7,017,393 B2 * | 3/2006 | Doe et al. | 73/54.28 |

* cited by examiner

*Primary Examiner*—Hezron Williams
*Assistant Examiner*—Tamiko D Bellamy
(74) *Attorney, Agent, or Firm*—Aslan Baghdadi; Paul, Hastings, Janofsky & Walker LLP

(57) ABSTRACT

A method of calibrating the torque outputs of a rheometer by using a calibrating object with a certified moment of inertia, measuring the moment of inertia of the calibrating object using the rheometer, and calculating the torque adjustment factor by dividing the certified moment of inertia value by the measured moment of inertia value. The torque adjustment factor is applied to correct subsequent measurements of rheological properties conducted using the rheometer. The torque adjustment factor may be double-checked for reproducibility by measuring the moment of inertia of the calibrating object, correcting it with the torque adjustment factor, and comparing it with its certified moment of inertia value.

35 Claims, 2 Drawing Sheets

RHEOMETER TORQUE CALIBRATION FIXTURE

This application claims the benefit of U.S. Provisional Application No. 60/815,566, filed Jun. 22, 2006, which is herein incorporated by reference in its entirety.

BACKGROUND

1. Field of the Invention

The present invention relates generally to the calibration of rheometers, which are used to characterize materials by measuring the materials' viscosity, elasticity, shear thinning, yield stress, compliance and/or other material properties. More particularly, the invention relates to calibrating the torque output of a rheometer.

2. Background of the Invention

Rheometers, viscometers or viscosimeters are typically used to measure fluid or other properties of materials, such as their viscosity, compliance, and modulus, by rotating, deflecting or oscillating a measuring geometry in a material, either by applying a torque and measuring the resultant velocity or displacement, or by applying a velocity or displacement and measuring the resultant torque. The torque and velocity/displacement are used in conjunction with measuring geometry factors to determine the properties of the material. As used herein, the term "rheometer" shall mean rheometers, viscometers, viscosimeters and similar instruments that are used to measure the properties of fluid or similar (see list below) materials.

The term "measuring object" shall mean an object having any one of several geometries, including, for example, cones, discs, vanes, parallel plates, concentric cylinders and double concentric cylinders. The "materials" may be liquids, oils, dispersions, suspensions, emulsions, adhesives, biological fluids such as blood, polymers, gels, pastes, slurries, melts, resins, powders or mixtures thereof. Such materials shall all be referred to generically as "fluids" herein. More specific examples of materials include asphalt, chocolate, drilling mud, lubricants, oils, greases, photoresists, liquid cements, elastomers, thermoplastics, thermosets and coatings.

As is known to one of ordinary skill in the art, many different geometries may be used for the measuring object in addition to the cylinders, cones, vanes and plates listed above. The measuring objects may be made of; for example, stainless steel, anodized aluminum or titanium. U.S. Pat. No. 5,777,212 to Sekiguchi et al., U.S. Pat. No. 4,878,377 to Abel and U.S. Pat. No. 4,630,468 to Sweet describe various configurations, constructions and applications of rheometers.

The term "calibration" refers to the process of standardizing the rheometer by determining the deviation from an established standard so as to ascertain the proper correction factors for subsequent measurements. Calibration of measuring instruments is vitally important to maintaining the constancy and integrity of the measurements. As known to one of ordinary skill in the art, calibration should be performed whenever possible and to a traceable standard. For rheometers, calibration can be performed to correct measurements of temperature, velocity, displacement, geometry dimensions, and torque, but the present invention is related particularly to the calibration of the torque. The calibration of the torque measurements determines the accuracy and precision of calculated rheological parameters including viscosity, storage modulus, and loss modulus, which are all critically sensitive to the torque value.

Common methods of calibrating viscometers use calibration liquids with known viscosities to correct the measured torque outputs. U.S. Pat. No. 5,509,297 describes a calibration method that plots the viscosity against the measured torque over the range of expected viscosity of the test sample at a specified rotor speed to convert the measured torque into the true viscosity. Another method uses rotating spindles of various sizes depending on the expected viscosity range of the test sample, while taking into account the spindle size in calculating the corrected property value. Calibration methods that use various liquids to correct the viscosity measurements can be significantly and easily influenced by temperature, velocity/displacement, geometry, dimensions, as well as torque in addition to being acutely susceptible to filling errors and contamination.

Other calibration approaches use weights of traceable mass together with either lines and pulleys or strain gauges to calibrate the torque values of rheometers. One proposal to the American Standard of Testing Materials ("ASTM") for developing a standard for calibration or conformance demonstration for rheometers for the measurement of torque employs a variant form of the line and pulley technique. FIG. 1 is a schematic perspective view of a rotary rheometer 100, showing torque measurement transducer 101, weight of traceable mass 102, line 103 connected to the weight 102, pulley 104, and test fixture 105. The ASTM proposal mounts the test fixture 105 to the bottom of the torque measurement transducer 101 so that the line 103 connected to the weight of traceable mass 102 transmits the force of the mass 102 to the test fixture 105 and the torque measurement transducer 101. The force thus applied produces a measurable torque value, which is then compared to the torque calculated from the applied force. The ratio between the torque output and the applied torque is used to calculate a calibration coefficient to correct subsequent torque measurements.

Calibration methods that use lines, pulleys, or strain gauges tend to be susceptible to both operator errors and systematic errors. For example, the line and pulley method described above requires the operator to make sure that the mass is free hanging without obstruction and that it is not swinging from side to side. Consequently, the need for an experienced operator to perform calibrations increases the costs of operation. In addition, prior art methods are susceptible to various sources for friction that can undermine the accuracy of the calibration and hence the constancy of the instrument. For example, attaching a line to the drive shaft or the torque measurement transducer in rheometers can side-load the shaft bearings, thus creating undesirable interactions with other bearings to produce friction. Even though strain gauges have been used to calibrate torque of rheometers, they are relatively expensive and are therefore not readily available for many rheometer users.

As seen by ASTM's recent interest in the torque calibration of rheometers, there exists a need to develop a simple yet accurate torque calibration technique for rheometers to increase the accuracy of the instrument while reducing sources of friction, costs of equipments, and level of skills required for calibration so that users of rheometers may afford and use their own calibration equipments whenever needed.

SUMMARY OF THE INVENTION

The present invention utilizes a process of torque calibration for rheometers by using a calibrating object with a certified moment of inertia ("MOI"), measuring the MOI of the calibrating object using the rheometer, and calculating the torque adjustment factor by dividing the certified MOI value by the measured MOI value. The torque adjustment factor is then applied to correct subsequent rheological measurements taken using the rheometer.

A preferred embodiment of the present invention is to double-check the reproducibility of the torque adjustment factor by measuring the MOI of the calibrating object again, applying the torque adjustment factor to correct the measured MOI, and comparing the corrected MOI with the certified MOI of the calibrating object. A preferred embodiment of the present invention is to calculate the percentage error between the measured MOI with the certified MOI. An exemplary embodiment is to select the dimensions and shape of the calibrating object so that the percentage error is less than one percent.

An exemplary embodiment of the present invention consists of a computer system with a display device and/or an input device. The computer system may comprise of an algorithm to calculate different rheological properties such as the MOI and the viscosity. The display device shows the values of rheological properties measured or calculated by the rheometer, including the torque value and the MOI value. The input device permits the user to enter certain data, such as the certified MOI of the calibrating object.

A preferred embodiment of the present invention is to clean the calibrating object and check that it is undamaged before using it for calibration. Another preferred embodiment is to repeat the method of calibrating the rheometer with calibrating objects of various moments of inertia to obtain multiple torque adjustment factors for a range of moments of inertia.

A preferred embodiment of the present invention uses calibrating objects so that the ratio of the MOI of the calibrating object to the MOI of the rheometer is at least ten to one. A preferred embodiment is to have a ratio of at least twenty to one. Another preferred embodiment is to have a ratio of at least thirty to one.

An exemplary embodiment of the present invention uses metal objects with moments of inertia calibrated by traceable means as the calibrating objects. A preferred embodiment uses a stainless steel disk or cylinder. Both the disk and the cylinder are advantageous over other shapes due to lower frictional resistance in air. Further preferred embodiment of the present invention uses a stainless steel disk that has a diameter of about 75 to 100 mm (for example, about 90 mm) and a thickness of about 8 to 12 mm (for example, about 10 mm).

The calibration method and apparatus described herein have many advantages over existing art. Instead of calibrating a dependent property like viscosity, the present invention calibrates the rheometer's torque output, which can be used to calculate other dependent properties. Consequently, the torque values and all dependent properties are guaranteed a certain degree of accuracy and precision depending on the precision of the torque adjustment factor. Unlike calibration methods based on viscosity or other properties, which are often significantly dependent upon temperature and velocity/displacement, the MOI and torque can be more accurately measured to a traceable standard with the rheometer.

The metal disk or cylinder used as the calibrating object is also less susceptible to contamination and filling errors than calibration liquids. Another advantage of the present invention is that it is not susceptible to various sources of friction that often produce significant errors in prior art calibration methods. The present invention also simplifies the calibration process so that owners of rheometers may purchase their own calibration equipment and perform calibrations whenever necessary, consequently reducing the cost of service engineers while improving the accuracy of the measured properties.

The features and advantages of the present invention will be more fully appreciated upon a reading of the following detailed description.

DETAILED DESCRIPTION OF THE INVENTION

Figure 1:
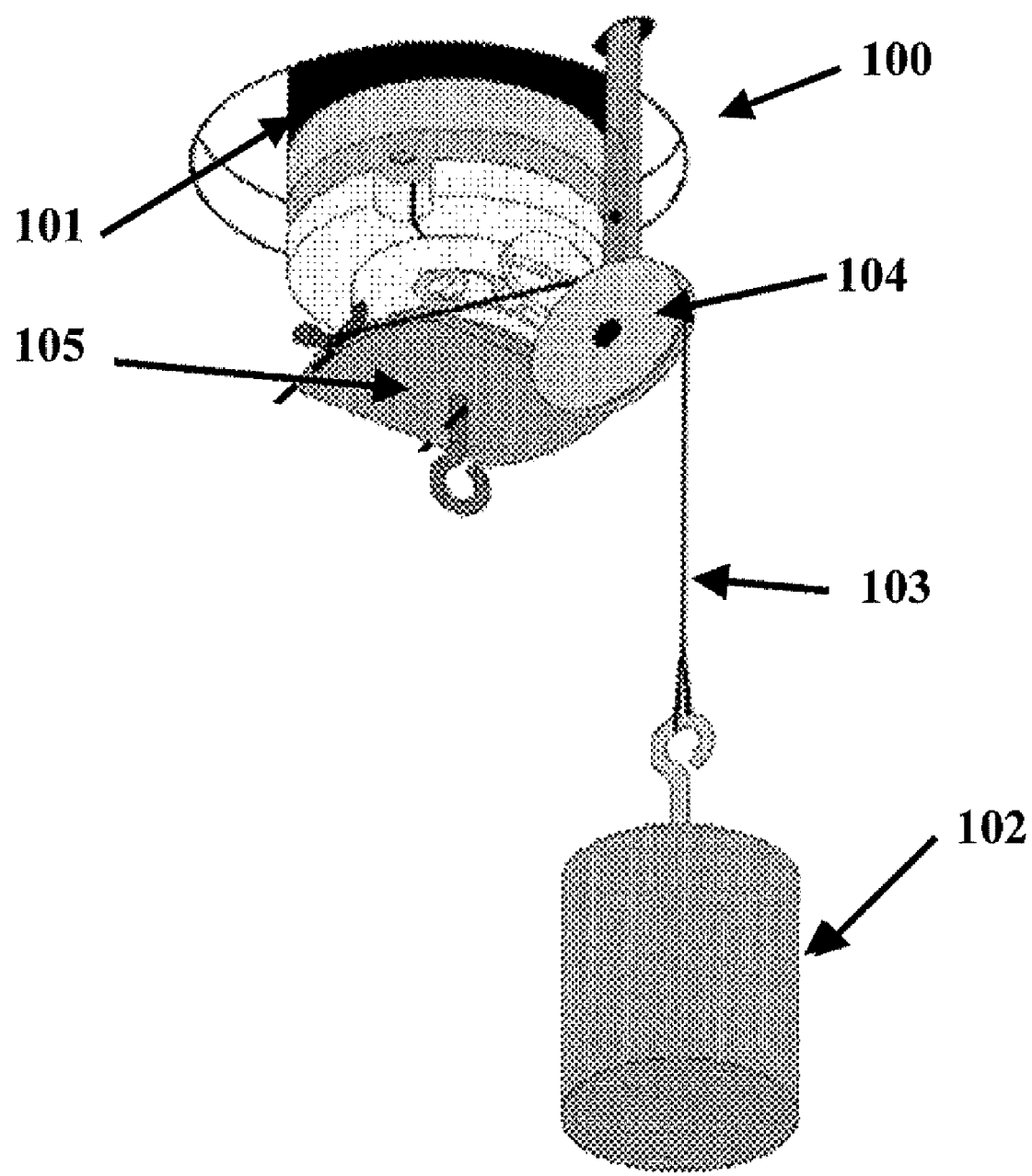
FIG. 1 is a schematic diagram of a perspective view of a prior art rheometer with a line and pulley system set up for calibration.
Figure 2:
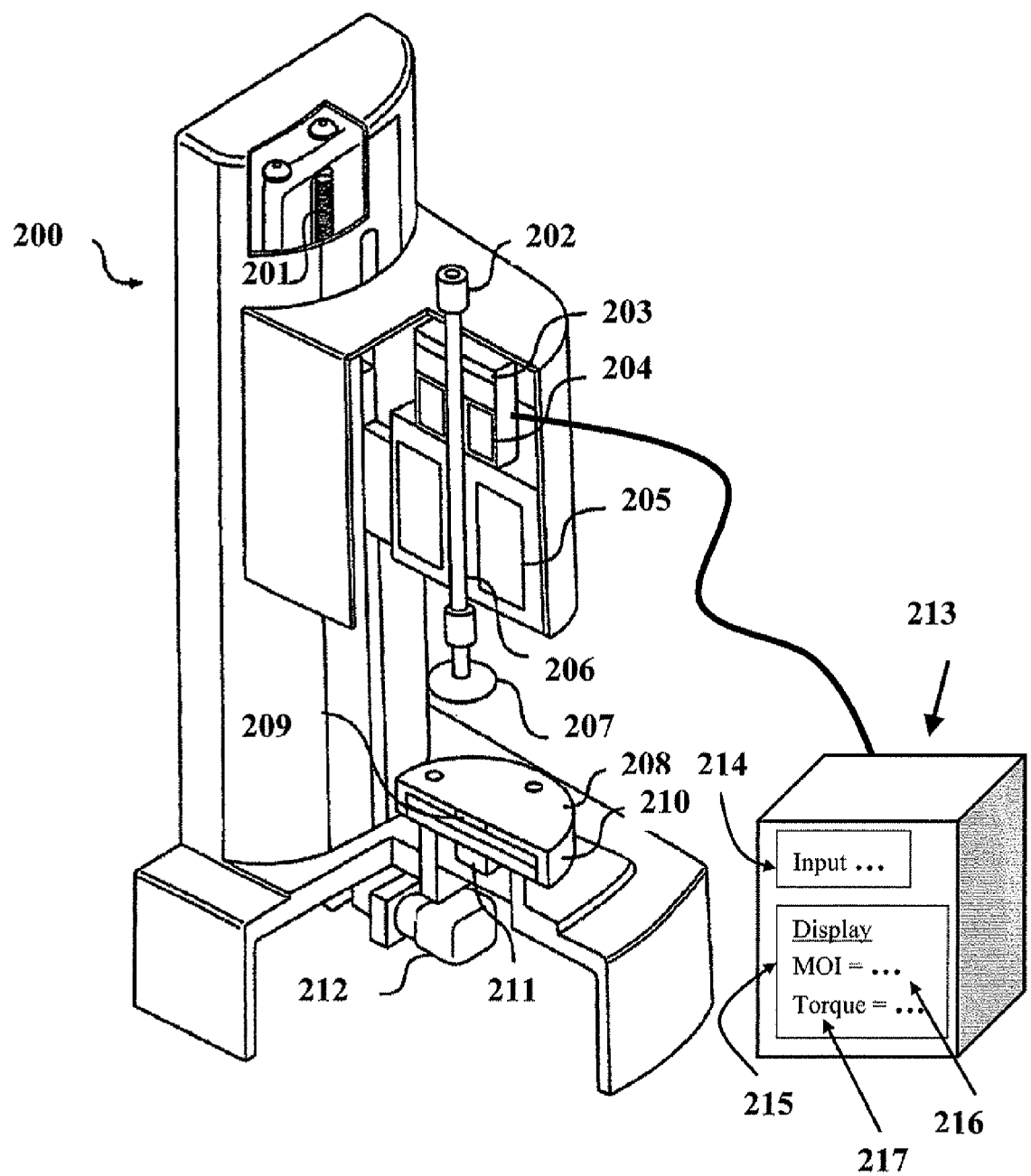
FIG. 2 is a schematic diagram of a rotary rheometer with an attached computer system consisting of an input device and a displaying device.

FIG. 2 is a schematic perspective view of a rotary rheometer 200, showing lead screw 201, draw rod 202, optical encoder 203, air bearing 204, drag cup motor 205, drive shaft 206, measuring object 207, surface 208, temperature sensor 209, heating/cooling assembly 210, normal force transducer 211, and auto gap set motor and encoder 212. The drag cup motor 205 contains a current in its coils to generate and apply a torque to the drive shaft 206. The torque in the drive shaft 206, in turn, applies torque to the measuring object 207. An exemplary embodiment of the invention has a computer system 213, which is herein used to mean any assembly of at least one type of device that is programmable or capable of receiving inputted data, storing data, performing calculations, or displaying data. The computer system 213 may be equipped with an algorithm to calculate different rheological properties such as the MOI and the viscosity. The computer system 213 may comprise a display device 215 such as a monitor that displays a moment of inertia ("MOI") signal 216 and a torque signal 217 of the measuring object 207. The computer system 213 may also consist of an input device 214 such as a keyboard.

The amount of torque applied depends on the current applied to the drag cup motor so the combined motor transducer rheometer 200 measures the motor torque from the energy input to the drag cup motor 205. The optical encoder 203 is capable of accurately measuring the angular displacement or angular acceleration of the measuring object 207. The rheometer 200, by using the equation: Torque=Moment of inertia*Angular Acceleration, is then capable of calculating the MOI of the measuring object 207 from the applied torque and the angular acceleration or the angular displacement of the calibrating object.

The present invention facilitates the calibration of rheometers by using a measuring object, hereby identified as the calibrating object, with a certified MOI value to obtain a correction factor for torque outputs. The certified MOI value of the calibrating object can be recorded as $I_c$. Before fitting the calibrating object to the rheometer 200, the MOI of the rheometer is measured and recorded as $I_r$. The calibrating object is then attached to one end of the drive shaft 206 of the rheometer 200. The MOT of the rheometer with the attached calibrating object is measured and recorded as $I_{total}$. Using the equation, MOI of Calibrating Object=$I_{total}-I_r$, the MOI of the calibrating object is calculated and recorded as $I_d$. The torque adjustment factor is then calculated as $I_c I_d$, recorded as $\tau_c$, and used to correct subsequent rheological measurements conducted by the rheometer 200.

Various rheometers may benefit from the teachings of the present invention. Exemplary rheometers include, for example, those described in U.S. Pat. Nos. 6,588,254 and 6,952,950 to Foster et al., which are all incorporated by reference herein. Such exemplary rheometers and other kinds of combined motor and transducer ("CMT") rheometers may benefit from incorporating the calibration technique of the present invention to simplify the need of service engineers, reduce the costs of calibration, and gain assurance of the accuracy and precision of the measurement of the output torque and its dependent properties.

A preferred embodiment of the present invention comprises a step of double-checking the reproducibility of the torque adjustment factor after the torque adjustment factor has been applied to subsequent rheological values measured by the rheometer. The double-checking step comprises measuring the MOI of the calibrating object, including applying the torque adjustment factor to the MOI, and comparing the measured MOI with the certified MOI of the calibrating object. Another preferred embodiment of the present invention is to calculate the percentage error between the measured MOI with the certified MOI of the calibrating object. An exemplary embodiment is to select the dimensions and shape of the calibrating object so that the percentage error is less than one percent. Another exemplary embodiment of the present invention comprises an input device 214 that permits the user to enter the certified MOI of the calibrating object.

The certified MOI of the calibrating object may be obtained through various methods or calculations. Certification companies such as Space Electronics LLC in Berlin, Connecticut utilize high precision MOI-measuring instruments to determine the MOI so that the value may be traceable to the standards of National Institute of Standards and Technology. Another method to determine MOI is to calculate the MOT from accurate measurements of the dimensions and the density of the object. Depending on the shape of the object and the axis it is rotating on, the equation for MOI differs. For example, a cylinder's MOI while rotating on the cylindrical or circular axis is obtained from the equation: MOI (cylinder)=$(1/2)*m*r^2$, where r is the radius and m is the mass of the cylinder. For a rectangular section spoke rotating on the same axis, MOI (rectangle)=$(1/3)*m*(L^2 0.25*W^2)$, where m is the mass, L is the length, and W is the width of the rectangular spoke. For a circular ring rotating on the cylindrical or circular axis, MOI (circular ring)=$(1/2)*\pi*\rho*h*(r_o^4 - r_i^4)$, where $\pi$ is a mathematical constant, $\rho$ is the density of the material, h is the height of the ring, $r_o$ is the radius of the outer ring and $r_i$ is the radius of the inner ring. If this method is employed to determine the MOI, the density of the object must be homogeneous throughout. One of ordinary skill in the art would readily b able to write computer programs to calculate the MOI of various objects, including the calibrating object of the present invention, from these equations. The discrepancy between the moments of inertia calculated from the geometric equations and from certification agencies are usually less than one percent. Therefore, the present invention can be implemented using either method to certify the moments of inertia of the calibrating object.

A preferred embodiment of the present invention further includes cleaning the calibrating object and checking that it is undamaged before attaching it to the shaft. Another preferred embodiment is to repeat the method of calibrating the rheometer by using calibrating objects with moments of inertia in different ranges to obtain multiple torque adjustment factors so that the proper $\tau_c$ can be used to correct measurements of materials within a specific MOI range.

In a preferred implementation of the present invention, the calibrating object is selected so that the ratio of the MOI of the calibrating object to the MOI of the rheometer is at least ten to one. In another implementation, a ratio of at least twenty to one is employed. In still another preferred implementation, a ratio of at least thirty to one is employed.

Preferred embodiments of the present invention use metal objects that have had their moments of inertia calibrated by traceable means as the calibrating object. For example, stainless steel disks and cylinders may be used. A disk is preferable because of its constant thickness and the relative ease of fitting a disk to the end of the drive shaft 206. Both cylinders and disks have the advantage over other shapes of reduced air friction that may affect the measurement of the MOI. Stainless steel is preferable because its hardness prevents the disk from being deformed. Also, stainless steel can be polished to have highly precise dimensions, compared to softer materials such as brass or aluminum. A preferred embodiment of the present invention uses stainless steel disks that have diameters of about 75 to 100 mm and thicknesses of about 8 to 12 mm.

The calibration method and apparatus described herein have many advantages over existing art. One advantage is that the present invention reduces the sources of friction and the costs of equipment that tend to produce calibration errors in prior art forms of calibration. The method disclosed herein also simplifies the calibration process so that owners of rheometers may purchase their own calibration equipments and perform calibrations easily and whenever necessary.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

What is claimed is:

1. A method of calibrating a rheometer comprising:
   obtaining a calibrating object with a certified moment of inertia calibrated by traceable means;
   recording the certified moment of inertia of the calibrating object;
   measuring a moment of inertia of the rheometer;
   recording the moment of inertia of the rheometer;
   fitting the calibrating object to one end of a drive shaft of the rheometer;
   measuring a total moment of inertia of the rheometer with the calibrating object fitted to the drive shaft;
   recording the total moment of inertia of the rheometer with the calibrating object fitted to the drive shaft;
   calculating a moment of inertia of the calibrating object by subtracting the moment of inertia of the rheometer from the total moment of inertia of the rheometer with the calibrating object fitted to the drive shaft;
   recording the moment of inertia of the calibrating object;
   calculating a torque adjustment factor by dividing the certified moment of inertia of the calibrating object by the moment of inertia of the calibrating object;
   recording the torque adjustment factor;
   applying the torque adjustment factor to subsequent rheological values measured using the rheometer.

2. The method of claim 1, further comprising cleaning the calibrating object and checking that the calibrating object is undamaged before fitting the calibrating object to the shaft.

3. The method of claim 1, further comprising inputting the calibrated moment of inertia of the calibrating object into an input device of a computer system.

4. The method of claim 1, further comprising displaying the torque adjustment factor in a display device of a computer system.

5. The method of claim 1, wherein the ratio of the moment of inertia of the calibrating object to the moment of inertia of the rheometer is at least ten to one.

6. The method of claim 1, wherein the calibrating object is a metal object.

7. The method of claim 6, wherein the metal object is a metal disk or cylinder.

8. The method of claim 6, wherein the metal object is a stainless steel disk or cylinder.

9. The method of claim 8, wherein the metal object is a stainless steel disk having a diameter of about 70 to 100 mm and a thickness of about 8 to 12 mm.

10. The method of claim 1, further comprising repeating the method of calibrating the rheometer by using calibrating objects with moments of inertia in different ranges.

11. The method of claim 10, further comprising obtaining multiple torque adjustment factors for different moment of inertia ranges, selecting an appropriate torque adjustment factor from the multiple torque adjustment factors, and applying the torque adjustment factor to subsequent rheological values measured using the rheometer.

12. The method of claim 1, further comprising double-checking the reproducibility of the torque adjustment factor.

13. A method of calibrating a rheometer comprising:
measuring a moment of inertia of the rheometer;
fitting a calibrating object with a certified moment of inertia calibrated by traceable means to one end of a drive shaft of the rheometer;
measuring a total moment of inertia of the rheometer with the calibrating object fitted to the drive shaft;
calculating a moment of inertia of the calibrating object by subtracting the moment of inertia of the rheometer from the total moment of inertia of the rheometer with the calibrating object fitted to the drive shaft;
calculating a torque adjustment factor by dividing the certified moment of inertia of the calibrating object by the moment of inertia of the calibrating object; and
applying the torque adjustment factor to subsequent rheological values measured using the rheometer.

14. The method of claim 13, further comprising after applying the torque adjustment factor to subsequent rheological values measured using the rheometer,
measuring the moment of inertia of the calibrating object, including applying the torque adjustment factor to the moment of inertia of the calibrating object; and
comparing the measured moment of inertia of the calibrating object to the certified moment of inertia of the calibrating object.

15. The method of claim 14, further comprising cleaning the calibrating object and checking that the calibrating object is undamaged before measuring the moment of inertia of the calibrating object.

16. The method of claim 14, further comprising calculating a percentage error between the measured moment of inertia of the calibrating object and the certified moment of inertia of the calibrating object.

17. The method of claim 15, wherein the dimensions and shape of the calibrating object are selected so that the percentage error is less than one percent.

18. The method of claim 13, further comprising cleaning the calibrating object and checking that the calibrating object is undamaged before fitting the calibrating object to the shaft.

19. The method of claim 13, further comprising inserting the calibrated moment of inertia of the calibrating object to an input device of a computer system.

20. The method of claim 13, further comprising displaying the torque adjustment factor in a display device of a computer system.

21. The method of claim 13, wherein the ratio of the moment of inertia of the calibrating object to the moment of inertia of the rheometer is at least ten to one.

22. The method of claim 13, wherein the calibrating object is a metal object.

23. The method of claim 22, wherein the metal object is a metal disk or cylinder.

24. The method of claim 22, wherein the metal object is a stainless steel disk or cylinder.

25. The method of claim 24, wherein the stainless steel disk has a diameter of about 70 to 100 mm and a thickness of about 8 to 12 mm.

26. The method of claim 13, further comprising repeating the method of calibrating the rheometer by using calibrating objects with moments of inertia in different ranges.

27. The method of claim 26, further comprising obtaining multiple torque adjustment factors for different moment of inertia ranges, selecting an appropriate torque adjustment factor from the multiple torque adjustment factors, and applying the torque adjustment factor to subsequent rheological values measured using the rheometer.

28. A rheometer, comprising:
a drive shaft;
a drag cup motor to rotate the drive shaft;
means for measuring the torque applied to the drive shaft;
a calibrating object with a certified moment of inertia calibrated by traceable means attached to one end of the drive shaft;
means for measuring the angular acceleration or the angular displacement of the drive shaft and the calibrating object; and
means for calculating the moment of inertia of the rheometer and the calibrating object.

29. The rheometer of claim 28, wherein the calibrating object is a metal object.

30. The rheometer of claim 29, wherein the metal object is a metal disk or cylinder.

31. The rheometer of claim 28, wherein the metal object is a stainless steel disk or cylinder.

32. The rheometer of claim 31, wherein the stainless steel disk has a diameter of about 75 to 100 mm and a thickness of about 8 to 12 mm.

33. The rheometer of claim 28, further comprising a computer system.

34. The rheometer of claim 33, wherein the computer system comprises an input device.

35. The rheometer of claim 34, wherein the computer system comprises a displaying device.

* * * * *